(12) United States Patent
Salmon et al.

(10) Patent No.: US 6,607,738 B2
(45) Date of Patent: *Aug. 19, 2003

(54) CHEMICAL COMPOSITION

(75) Inventors: Michael Salmon, Frome (GB); Sandra Sidney, Gosport (GB); Dene Clifford Godfrey, Pontyclun (GB)

(73) Assignees: Nipa Laboratories, LTD., Skillman, NJ (US); Johnson & Johnson Consumer Companes, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/064,189

(22) Filed: Apr. 22, 1998

(65) Prior Publication Data

US 2001/0043936 A1 Nov. 22, 2001

(51) Int. Cl.$^7$ .............. A01N 25/34; A01N 25/00; A61K 4/00
(52) U.S. Cl. .............. 424/402; 424/400; 424/405; 514/844; 514/938
(58) Field of Search .............. 424/400, 405, 424/402; 514/844, 938

(56) References Cited

U.S. PATENT DOCUMENTS 5,422,112 A * 6/1995 Williams .............. 424/401
5,536,305 A * 7/1996 Yu .............. 106/18.33
5,733,362 A * 3/1998 Hahn .............. 106/18.33

FOREIGN PATENT DOCUMENTS

| EP | 0 773 281 A2 | 9/1996 |
| EP | 763341 | 3/1997 |
| EP | 0763341 | 4/1997 |
| HU | 208236 | 9/1993 |
| WO | WO 9624329 | 8/1996 |
| WO | WO 97/20464 | 6/1997 |

OTHER PUBLICATIONS

Formulating With Glycacil® and Phenoxyethanol: The Non-formaldehyde alternative to Paraben?; Lonza Publication: Dec. 1995.

Hungarian Search Report for Hungarian Appln. No. P 00 01850 dated Jan. 16, 2001.

* cited by examiner

*Primary Examiner*—Jose' G. Dees
*Assistant Examiner*—Robert M DeWitty
(74) *Attorney, Agent, or Firm*—Michele G. Mangini

(57) ABSTRACT

A preservative system comprising iodopropynyl butyl carbamate and phenoxyethanol at a weight ratio of iodopropynyl butyl carbamate to phenoxyethanol within the range of about 1:90 to about 1:400 shows a broad anti-microbial effect and can permit use of the preservative system at a low level in end use products such as personal care products.

22 Claims, No Drawings

CHEMICAL COMPOSITION

The present composition relates to a chemical composition comprising a preservative system and to a method of making and a use of such a chemical composition. Particularly although not exclusively the present invention relates to a chemical composition comprising a personal care product including a preservative system.

Personal care products come in many different forms. They include creams, lotions, pastes, liquids, aerosols, shampoos, gels, wipes, bars, sticks, powders and granules any or all of which are intended for topical application to the skin including the scalp and the mucosa including the lips.

The products are generally designed to have a substantial shelf life. The products need to be manufactured at one site, transported possibly over considerable distance to a depot or other storage facility prior to further transport to a point of sale. The product may then spend considerable time on a retailer's shelf prior to purchase and further storage by the user whether for individual use or use in for example a hotel, workplace, institution or the like. All of such storage will take place under uncontrolled conditions including considerable variation in temperature.

In order to keep microbiological and fungal growth in such products at an acceptable level it is conventional practice for the products to contain a preservative. Many preservatives are available. The appropriate preservative has to be selected with regard to its efficacy and its acceptability to contact with human or animal skin. With regard to its acceptability there are in many countries laws and regulations governing the maximum permitted content of preservative in products intended for human use due to their possible toxic or otherwise harmful effect.

The need to control microbiological growth in personal care products is known to be particularly acute in water based products such as non-ionic oil-in-water emulsions and in pre-impregnated wipes such as baby wipes.

It is an object of the present invention to provide an effective preservative system permitting its use at low levels.

It is a further object of the present invention to provide a personal care product containing an effective preservative system at a low level.

It is yet a further object of the present invention to provide a wipe intended for personal use pre-impregnated with a non-ionic oil-in-water emulsion and containing an effective preservative system at a low level.

According to a first aspect of the present invention there is provided a chemical composition comprising a preservative system comprising iodopropynyl butyl carbamate and phenoxyethanol at a weight ratio of iodopropynyl butyl carbamate to phenoxyethanol within the range of about 1:90 to about 1:400.

Such a preservative system can show a synergistic preservative action greater than would be expected from the two components acting independently. This synergistic action can produce a broad anti-microbial effect and can permit use of the preservative system at a low level in end use products such as personal care products. Use of the preservative at a low level can lead to cost savings and can reduce the chance of any untoward reactions between the preservative system and the skin of a user of a personal care product containing the preservative system.

The efficacy of the present preservative system containing a maximum of one part of iodopropynyl butyl carbamate to 90 parts phenoxyethanol is surprising. A known preservative system ex Lonza advocates the use of iodopropynyl butyl carbamate as a 10 wt % solution in PEG-4 laurate in combination with phenoxyethanol at a minimum ratio of one part iodopropynyl butyl carbamate per se to 70 parts phenoxyethanol at a total level of the preservative system in for example a shampoo of at least 1 wt %. The present invention requires a lower ratio of iodopropynyl butyl carbamate to phenoxyethanol, avoids the need for PEG-4 laurate or EDTA and yet can provide effective anti-microbial action at a comparatively lower level of use in a personal care product.

The present chemical composition can moreover provide a broad anti-microbial effect without the use of formaldehyde donors or paraben derived products. These traditional preservatives have been widely used in the past but are now no longer permitted in a number of countries for products intended for human use.

Preferably the present chemical composition comprises a preservative system wherein the weight ratio of iodopropynyl butyl carbamate to phenoxyethanol lies within the range of about 1:90 to about 1:200. Preferably the iodopropynyl butyl carbamate is dissolved in the phenoxyethanol. More suitably the preservative system comprises a 0.7% wt solution of iodopropynyl butyl carbamate in phenoxyethanol.

The present preservative system can conveniently be supplied to a manufacturer as a ready dissolved solution of iodopropynyl butyl carbamate in phenoxyethanol. Even more conveniently the preservative system can be supplied in premeasured dosed quantities.

Preferably the present chemical composition comprises additionally a personal care product. Suitably the chemical composition comprises the preservative system present in the personal care product at a level between 0.15 and 1.00 wt % with respect to the total weight of the chemical composition. More suitably the chemical composition comprises the preservative system present in the personal care product at a level between 0.25 and 0.60 wt % with respect to the total weight of the chemical composition.

According to another aspect of the present invention there is provided a personal care product containing with respect to the final composition weight between 0.15 and 1.00 wt % of a preservative system comprising a solution of iodopropynyl butyl carbamate in phenoxyethanol at a weight ratio of iodopropynyl butyl carbamate to phenoxyethanol within the range of about 1:90 to about 1:400. Preferably the preservative system is present at between 0.25 and 0.60 wt % with respect to the final composition weight.

Personal care products suitable for use in the present invention can be in any form and can include creams, lotions, pastes, liquids, aerosols, shampoos, gels, wipes, bars, sticks, powders and granules any or all of which are intended for topical application to the skin including the scalp and the mucosa including the lies.

It is understood that the present invention extends to a wipe or wipes impregnated with the present chemical composition. In such an embodiment of the present invention the level of preservative system present is measured with respect to the chemical composition impregnated on to the wipe, not with respect to the total weight of the personal care product including the wipe or wipes.

The personal care product can be aqueous based such as an oil-in-water emulsion. The present invention is deemed particularly suitable for a wipe, such as contained in a tub or sachet of baby wipes, impregnated with a non-ionic oil-in-water emulsion.

According to another aspect of the present invention there is provided use of a chemical composition comprising a preservative system comprising iodopropynyl butyl carbamate and phenoxyethanol at a weight ratio of iodopropynyl butyl carbamate to phenoxyethanol within the range of about 1:90 to about 1:400 in preserving a personal care product.

According to another aspect of the present invention there is provided a method for making a chemical composition comprising a preservative system comprising admixing iodopropynyl butyl carbamate and phenoxyethanol at a weight ratio of iodopropynyl butyl carbamate to phenoxyethanol within the range of about 1:90 to about 1:400, preferably within the range of about 1:90 to 1:200.

The present preservative system can be prepared by dissolving the iodopropynyl butyl carbamate in phenoxyethanol at the required ratio. Gentle heating up to 40° C. can be employed if desired. Suitably the present method comprises a preservative system comprising a 0.7 wt % solution of iodopropynyl butyl carbamate in phenoxyethanol.

The preservative system can be incorporated in a personal care product as part for example of a conventional manufacturing process. Other features of the present method are as given above.

Embodiments of the present invention will now be described by way of example only.

A batch of a cream formulation comprising an oil-in-water emulsion containing 7.5 wt % Crodex A (an emulsifying wax ex-Croda Chemicals), 5.0 wt % propylene glycol and 87.5 wt % sterile water was prepared using a homogenising mixer.

Such a formulation represents the basis of a simple body lotion, hand cream or the like.

Portions of the cream formulation were admixed with a preservative system comprising iodopropynyl butyl carbamate and phenoxyethanol at varying weight ratios of iodopropynyl butyl carbamate to phenoxyethanol. In each case the content of the iodopropynyl butyl carbamate in the cream formulation was kept constant at a level of 0.0025 wt % with respect of the total weight of the formulation.

Each portion of the formulation was divided into two. One specimen was inoculated with $7.5 \times 10^7$ mixed bacteria per g of cream. The other specimen was inoculated with $2.4 \times 10^6$ mixed fungi per g of cream.

For each specimen the number of surviving organisms was determined at 0 hours, 25 hours and 72 hours after inoculation. The ratios of iodopropynyl butyl carbamate and phenoxyethanol employed and the results of the inoculation tests are given in Table I below.

TABLE I

| IPBC/PhOH Ratio | | 0 Hours | 24 Hours | 72 Hours |
|---|---|---|---|---|
| 1:5 | Mixed Bacteria | TNTC | TNTC | $1.4 \times 10^6$ |
| | Mixed Fungi | $2.4 \times 10^5$ | $1.4 \times 10^5$ | $1.3 \times 10^3$ |
| 1:10 | Mixed Bacteria | TNTC | $3.6 \times 10^6$ | $1.0 \times 10^6$ |
| | Mixed Fungi | $1.2 \times 10^5$ | $9.0 \times 10^4$ | $3.0 \times 10^2$ |
| 1:15 | Mixed Bacteria | $4.1 \times 10^6$ | $8.4 \times 10^5$ | $6.0 \times 10^5$ |
| | Mixed Fungi | $6.4 \times 10^4$ | $4.1 \times 10^4$ | <10 |
| 1:20 | Mixed Bacteria | $3.4 \times 10^6$ | $3.5 \times 10^5$ | $1.6 \times 10^5$ |
| | Mixed Fungi | $3.2 \times 10^4$ | $3.0 \times 10^4$ | <10 |
| 1:25 | Mixed Bacteria | $2.8 \times 10^6$ | $3.4 \times 10^5$ | $8.8 \times 10^4$ |
| | Mixed Fungi | $4.4 \times 10^4$ | $3.0 \times 10^4$ | <10 |
| 1:50 | Mixed Bacteria | $2.9 \times 10^6$ | $3.0 \times 10^5$ | $1.3 \times 10^4$ |
| | Mixed Fungi | $2.1 \times 10^4$ | $2.5 \times 10^5$ | <10 |
| 1:100 | Mixed Bacteria | $2.9 \times 10^6$ | $2.4 \times 10^5$ | $2.0 \times 10^3$ |
| | Mixed Fungi | $3.0 \times 10^4$ | $2.3 \times 10^4$ | <10 |
| 1:150 | Mixed Bacteria | $2.6 \times 10^6$ | $2.0 \times 10^3$ | <10 |
| | Mixed Fungi | $1.4 \times 10^4$ | $1.4 \times 10^4$ | <10 |
| 1:200 | Mixed Bacteria | $2.5 \times 10^6$ | <10 | <10 |
| | Mixed Fungi | $8.0 \times 10^3$ | $9.3 \times 10^3$ | <10 |
| 1:300 | Mixed Bacteria | $6.4 \times 10^6$ | <10 | <10 |
| | Mixed Fungi | $8.5 \times 10^5$ | $7.0 \times 10^4$ | <10 |
| 1:400 | Mixed Bacteria | $6.0 \times 10^6$ | <10 | <10 |
| | Mixed Fungi | $8.1 \times 10^5$ | $7.0 \times 10^4$ | <10 |
| 1:500 | Mixed Bacteria | $2.6 \times 10^6$ | <10 | <10 |
| | Mixed Fungi | $7.7 \times 10^5$ | $6.0 \times 10^4$ | <10 |

TABLE I-continued

| IPBC/PhOH Ratio | | 0 Hours | 24 Hours | 72 Hours |
|---|---|---|---|---|
| 1:600 | Mixed Bacteria | $1.8 \times 10^6$ | <10 | <10 |
| | Mixed Fungi | $6.2 \times 10^5$ | $5.1 \times 10^4$ | <10 |
| 1:700 | Mixed Bacteria | $1.1 \times 10^6$ | <10 | <10 |
| | Mixed Fungi | $6.0 \times 10^5$ | $5.0 \times 10^4$ | <10 |

TNTC - Too Numerous to count
All results quoted in organisms surviving/g
IPBC is iodopropynyl butyl carbamate
PhOH is phenoxyethanol As control experiments portions of the cream formulation containing respectively no added preservative agents, iodopropynyl butyl carbamate at a level of 0.0025 wt % with respect to the whole formulation and no phenoxyethanol, and phenoxyethanol at varying levels and no iodopropynyl butyl carbamate were prepared and inoculated with the mixed bacteria and the mixed fungi at the levels employed in the specimens whose results are set out in Table I. The preservative employed and the results of the inoculation tests for these control experiments are given in Table II

TABLE II

| IPBC ppm | PhOH (ppm) | | | 0 Hours | 24 Hours | 72 Hours |
|---|---|---|---|---|---|---|
| 25 | 0 | Mixed Bacteria | TNTC | $1.8 \times 10^6$ | $2.9 \times 10^5$ |
| | | Mixed Fungi | $8 \times 10^5$ | $1.2 \times 10^5$ | $5.2 \times 10^4$ |
| 0 | 2500 | Mixed Bacteria | $8.1 \times 10^6$ | $3.3 \times 10^6$ | $2.6 \times 10^5$ |
| | | Mixed Fungi | $5.6 \times 10^5$ | $8.0 \times 10^4$ | $4.5 \times 10^4$ |
| 0 | 3750 | Mixed Bacteria | $6.4 \times 10^6$ | $2.9 \times 10^6$ | $9.0 \times 10^4$ |
| | | Mixed Fungi | $2.7 \times 10^5$ | $7.1 \times 10^4$ | $1.2 \times 10^4$ |
| 0 | 5000 | Mixed Bacteria | $6.3 \times 10^6$ | $2.5 \times 10^5$ | $8.0 \times 10^3$ |
| | | Mixed Fungi | $1.9 \times 10^5$ | $2.1 \times 10^4$ | $1.1 \times 10^4$ |
| 0 | 7500 | Mixed Bacteria | TNTC | $8.2 \times 10^5$ | $1.3 \times 10^2$ |
| | | Mixed Fungi | $7.2 \times 10^5$ | $2.6 \times 10^5$ | $1.4 \times 10^5$ |
| 0 | 10000 | Mixed Bacteria | $7.2 \times 10^6$ | $1.3 \times 10^3$ | <10 |
| | | Mixed Fungi | $7.0 \times 10^5$ | $8.5 \times 10^4$ | $6.4 \times 10^4$ |
| 0 | 12500 | Mixed Bacteria | $6.3 \times 10^6$ | <10 | <10 |
| | | Mixed Fungi | $7.0 \times 10^5$ | $7.0 \times 10^4$ | $1.0 \times 10^4$ |
| 0 | 15000 | Mixed Bacteria | $3.5 \times 10^6$ | <10 | <10 |
| | | Mixed Fungi | $6.8 \times 10^5$ | $6.5 \times 10^4$ | $6.0 \times 10^3$ |
| 0 | 17500 | Mixed Bacteria | $3.0 \times 10^6$ | <10 | <10 |
| | | Mixed Fungi | $6.6 \times 10^5$ | $3.2 \times 10^4$ | $5.8 \times 10^3$ |
| 0 | 0 | Mixed Bacteria | TNTC | TNTC | $8.2 \times 10^6$ |
| | | Mixed Fungi | TNTC | $6.2 \times 10^5$ | $5.2 \times 10^5$ |

2500 ppm Phenoxyethanol is the concentration used in the 1:100 ratio
3750 ppm Phenoxyethanol is the concentration used in the 1:150 ratio
5000 ppm Phenoxyethanol is the concentration used in the 1:200 ratio
7500 ppm Phenoxyethanol is the concentration used in the 1:300 ratio
10000 ppm Phenoxyethanol is the concentration used in the 1:400 ratio
12500 ppm Phenoxyethanol is the concentration used in the 1:500 ratio
15000 ppm Phenoxyethanol is the concentration used in the 1:600 ratio
17500 ppm Phenoxyethanol is the concentration used in the 1:700 ratio A comparison of the results given in Tables I and II shows that greater than expected performance is recorded for the combined preservative system relative to the contribution made by each preservative when present separately. Anti-fungal synergy is evident at ratios of IPBC:PhOH of 1:15 and upwards. Broad spectrum synergy with respect to both fungi and bacterial inoculation is evident at ratios of IPBC:PhOH in the range 1:90 to 1:400.

What is claimed is:

1. A personal care product comprised of a chemical composition comprised of a preservative system comprising an iodopropynyl butyl carbamate and phenoxyethanol at a weight ratio of iodopropynyl butyl carbamate to phenoxyethanol within the range of about 1:90 to about 1:400, whereby the iodopropynyl butyl carbamate and phenoxyethanol are present in an effective anti-microbial amount for a two component preservative system and said preservative system possesses synergistic preservative action properties.

2. The personal care product of claim 1, wherein the weight ratio of iodopropynyl butyl carbamate to phenoxyethanol lies within the range of about 1:90 to about 1:200.

3. The personal care product of claim 2, wherein the preservative system comprises about a 0.7 wt % solution of iodopropynyl butyl carbamate in phenoxyethanol.

4. The personal care product of claim 1, wherein the iodopropynyl butyl carbamate is dissolved in the phenoxyethanol.

5. The personal care product of claim 1, wherein the preservative system is supplied in premeasured dosed quantities.

6. The personal care product of claim 1 wherein the preservative system is present in the personal care product at a level between about 0.150 and about 1.000 wt % with respect to the total weight of the chemical composition.

7. The personal care product according to claim 6 wherein the preservative system is present in the personal care product at a level between about 0.25 and about 0.60 wt % with respect to the total weight of the chemical composition.

8. The personal care product according to claim 1 wherein the personal care product is aqueous based.

9. The personal care product according to claim 8 wherein the personal care product is an oil-in-water emulsion.

10. The personal care product according to claim 1 in the form of a non-ionic oil-in water emulsion impregnated onto a wipe.

11. A method of preserving a personal care product comprising: admixing iodopropynyl butyl carbamate and phenoxyethanol in a personal care product, whereby the iodopropynyl butyl carbamate and phenoxyethanol are present in an effective anti-microbial amount for a two component preservative system and the preservative system possesses synergistic preservative action properties.

12. A method for making a chemical composition comprising a preservative system comprising
   a) admixing iodopropynyl butyl carbamate and phenoxyethanol at a weight ratio of iodopropynyl butyl carbamate to phenoxyethanol within the range of about 1:90 to about 1:400, whereby the iodopynyl butyl carbamate and phenoxyethanol are present in an effective anti-microbial amount for a two component preservative system and the preservative system possesses synergistic preservative action properties; and
   b) incorporating the preservative system in a personal care product.

13. A method according to claim 12 wherein the weight ratio of iodopropynyl butyl carbamate to phenoxyethanol lies within the range of about 1:90 to about 1:200.

14. A method according to claim 13 wherein the preservative system comprises about a 0.7 wt % solution of iodopropynyl butyl carbamate in phenoxyethanol.

15. A method according to claim 12 comprising dissolving the iodopropynyl butyl carbmate in the phenoxyethanol.

16. A method according to claim 12 including incorporating the preservative system in a personal care product at a level between about 0.15 and about 1.00 wt % with respect to the total weight of the final composition.

17. A method according to claim 16 wherein the preservative system is incorporated in the personal care product at a level between about 0.25 and about 0.6 wt % with respect to the total weight of the final composition.

18. A method according to claim 12 wherein the personal care product is aqueous based.

19. A method according to claim 18 wherein the personal care product is an oil-in-water emulsion.

20. A method according to claim 19 further comprising impregnating a wipe with the personal care product, wherein the personal care product is a non-ionic oil-in-water emulsion.

21. The personal care product of claim 1 wherein the product is a wipe impregnated with the preservative system.

22. A method for making a personal care product comprising
   incorporating iodopropynyl butyl cerbamate and phenoxyethanol at a weight ratio of iodopropynyl butyl carbamate to phenoxyethanol within the range of about 1:90 to about 1:400 to the product, whereby the iodopropynyl butyl carbamate and phenoxyethanol are present in an effective anti-microbial amount for a two component preservative system and the preservative system possesses synergistic preservative action properties.

* * * * *